United States Patent [19]
Lichfield

[11] 4,303,605
[45] Dec. 1, 1981

[54] PRODUCTION OF LAYERED TOOTHPICKS

[76] Inventor: William H. Lichfield, Box 112, Corrine, Utah 84307

[21] Appl. No.: 159,484

[22] Filed: Jun. 16, 1980

[51] Int. Cl.³ .......................... B29C 17/02; B29D 7/18
[52] U.S. Cl. ........................................ 264/158; 132/93; 144/221; 144/323; 264/68; 264/163; 264/339; 264/DIG. 40; 425/DIG. 7
[58] Field of Search ................. 264/68, 103, 158, 163, 264/281, 339, DIG. 40; 425/DIG. 7; 132/89, 93; 144/221, 323; 409/131, 199, 309

[56] References Cited

U.S. PATENT DOCUMENTS

| | | | |
|---|---|---|---|
| 19,035 | 1/1858 | Mallary | 144/221 |
| 344,810 | 7/1886 | Boynton | 144/221 |
| 512,583 | 1/1894 | Hubbell et al. | 144/221 |
| 1,701,912 | 2/1929 | De Walt | 144/221 |
| 2,365,952 | 12/1944 | Hanson | 264/163 |
| 3,247,857 | 4/1966 | Kanbar | 132/93 |
| 3,494,304 | 2/1970 | Gugler | 264/339 |
| 3,795,964 | 3/1974 | Beckman | 264/339 |
| 3,879,063 | 4/1975 | de Man | 264/68 |
| 4,164,530 | 8/1979 | Renjilian et al. | 264/339 |

Primary Examiner—James B. Lowe
Attorney, Agent, or Firm—B. Deon Criddle

[57] ABSTRACT

A method and tool for making tapered, layered plastic toothpicks from a solid plastic slab wherein a rapidly rotating tool having a single cutting edge configured to simultaneously cut and roll a thin film of plastic into a toothpick of the desired shape with each complete revolution is brought into contact with the plastic slab at a predetermined angle.

9 Claims, 21 Drawing Figures

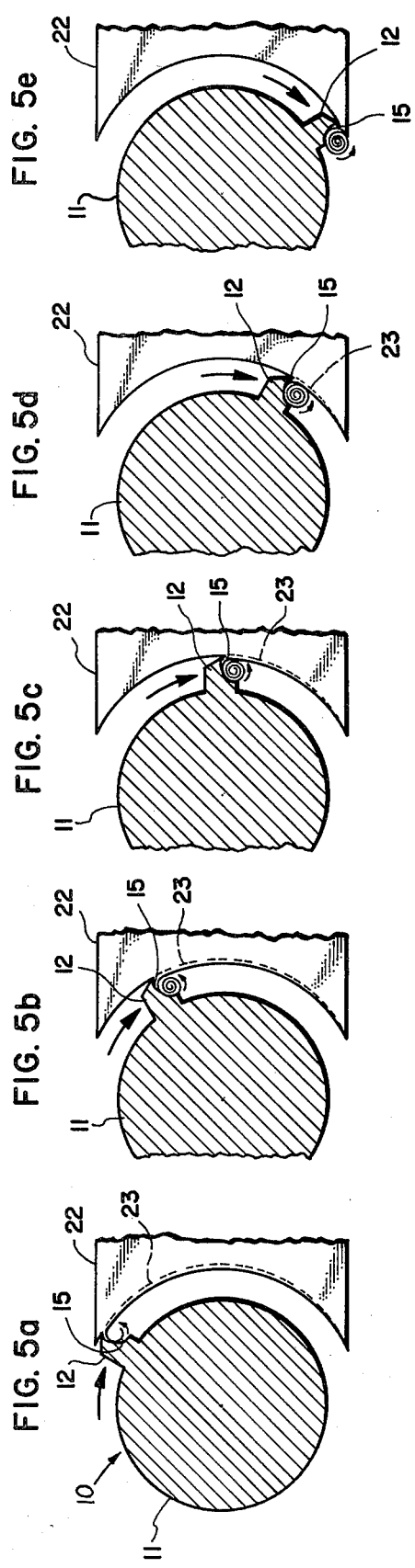
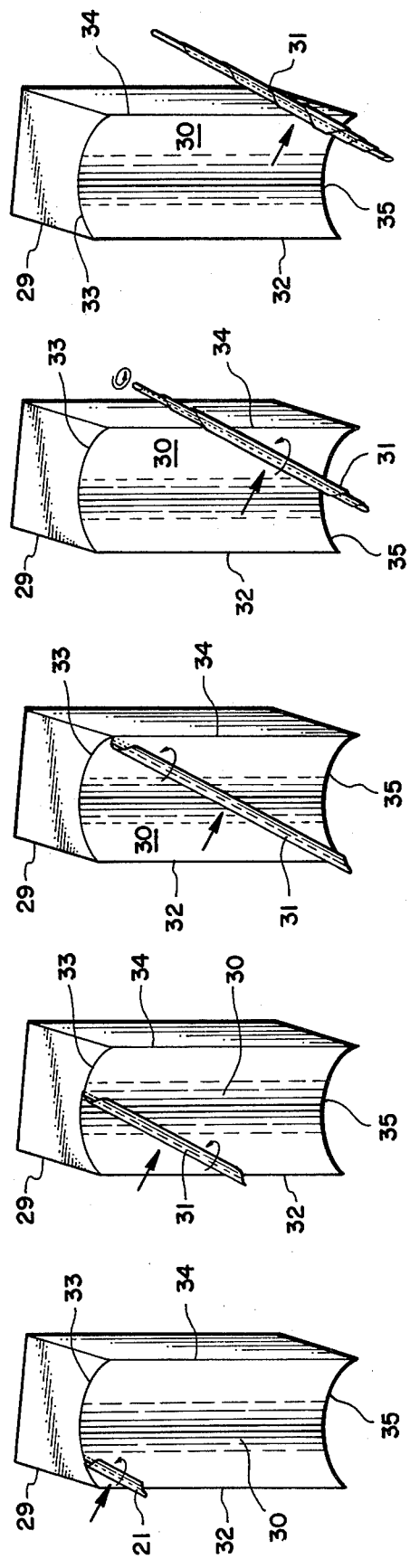

PRODUCTION OF LAYERED TOOTHPICKS

BACKGROUND OF THE INVENTION

This invention relates to a tool and method of using the tool to form layered, tapered plastic toothpicks. More particularly this invention relates to a rotary tool having a single cutting edge wherein the cutting surface is configured to simultaneously cut and roll a thin sheet of plastic from a solid plastic slab into a rolled layered and tapered toothpick.

Copending patent application Ser. No. 160,083, filed of even date herewith and entitled, "Therapeutic Toothpick" discloses and claims a novel toothpick which is made from a thin film of plastic which has been appropriately rolled to form a pliable toothpick which is layered and has a forwardly tapered front end having spiraling ridges formed from an edge of the rolled plastic. Such toothpicks are superior to conventional solid toothpicks in their ability to clean between teeth and extend into small crevices. Moreover, these toothpicks may be used to stimulate and massage gingival surfaces and to supply medicines or breath fresheners to the mouth. While these toothpicks can be hand rolled from thin plastic sheets, such a procedure is both time consuming and expensive. It would, therefore, the preferable to be able to automate the procedure by which the toothpicks are made.

OBJECTS AND SUMMARY OF THE INVENTION

It is an object of the present invention to provide a rotary tool for the formation of rolled plastic toothpicks from a solid plastic slab.

It is also an object of this invention to provide a tool which will simultaneously cut a thin plastic film from a solid plastic slab and form the film into a tightly rolled plastic toothpick of the desired configuration.

Another object of this invention is to provide a method of forming rolled plastic toothpicks on an automated basis such that a toothpick is cut, rolled and ejected from a plastic slab with each complete revolution of the cutting tool.

These and other objects may be accomplished by means of a cylindrical rotatable cutting and shaping tool having a single cutting lip which contains a recess running the length thereof. The cutting lip may be linear or helical on the surface of the tool depending upon the final shape of the toothpick to be formed. Prior to forming the toothpicks, the tool is firmly affixed to a milling machine or similar apparatus capable of adjustment so as to allow for positioning the cutting tool in a three dimensional x, y, z rectangular coordinate system to present the desired cutting angle. A slab of solid plastic is then moved in a fixed plane along the y axis of said system at a predetermined speed to come into contact with the prepositioned and rotating cutting tool. The cutting tool slices a thin film from the plastic slab. The edge of the film thus cut enters the recess in the tool lip adjacent the cutting edge and is caused to coil in a direction opposite the direction in which the cutting tool is rotating. As the tool rotates, the cut film within the recess continues to rotate and is tightly rolled. As the cutting lip rotates out of contact with the plastic, a completed rolled and tapered toothpick is ejected from within the recess by centrifugal force.

DRAWINGS OF THE INVENTION

FIGS. 5a to 5e is partial schematic cross-sectional view of a cutting tool cutting into a plastic slab showing the cutting pattern in phantom lines and also showing configuration of the lip recess and the rolling of the severed film within the recess.

FIGS. 9a to 9e are schematic step by step representations coinciding with FIGS. 5a to 5e showing how a helical cutting tool as shown in FIG. 3 cutting in the plastic block shown in FIG. 7 produces a toothpick which is rolled and tapered at both ends.

DETAILED DESCRIPTION OF THE INVENTION

Figure 1:
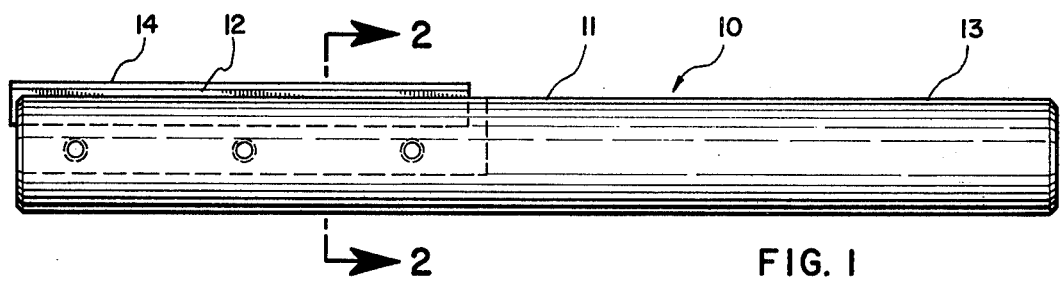
FIG. 1 is an elevational view of a cutting tool having a linear cutting lip.
Figure 2:
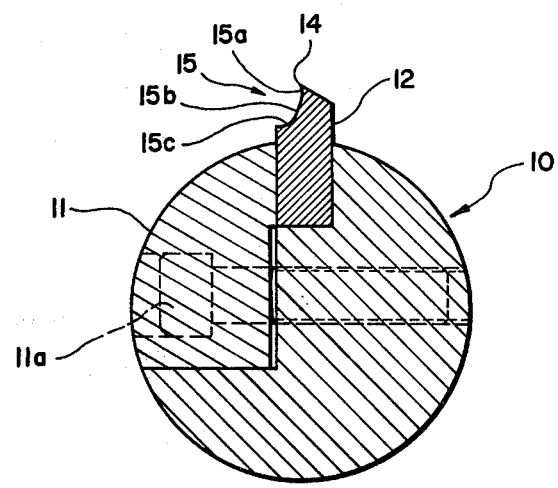
FIG. 2 is a cross-sectional view of the tool of FIG. 1 taken along lines 2—2 showing the cutting edge and lip recess.

FIGS. 1 and 2 show a tool 10 of the invention comprising a shaft 11 having a linear cutting lip 12 along a portion of the surface with the upper end 13 being of a size and shape that can be secured into the chuck of a milling or other appropriate machine. The lip 12 has a cutting edge 14, and immediately adjacent thereto is a recess 15. The diameter of tool 10 is preferably on the order of 800 to 1000 mils.

Recess 15 is configured to cause the severed plastic film to curl and be rolled within the recess. This recess must be sufficiently wide that it can handle the maximum toothpick diameter without distortion or jamming. However, if the recess is too wide, the toothpick may not be rolled as tightly as desired. It may, therefore, be necessary to determine the recess dimensions empirically for each toothpick produced. Generally speaking, toothpicks cut from a tool having a diameter of 0.8 to 1 inch cutting at a maximum depth of about 3 mils will have a diameter of about 40 to 80 mils when tightly rolled. The recess 15 does not necessarily have to accommodate the entire diameter of the toothpick but the configuration is critical. It has been found best to have the recess 15 depend downwardly and inwardly in an arcuate wall 15a from cutting edge 14 to the recess floor 15b. Floor 15b is relatively flat for a distance and then are upwardly and inwardly in an opposite wall 15c toward the shaft 11. Walls 15a and 15c do not necessarily have to follow the same curvature as wall 15a may have a tighter curvature than wall 15c. For toothpicks having a diameter of about 60 mils formed from a severed film having a maximum thickness of about 3 mils wall 15a curves downwardly and inwardly to floor 15b located about 25 plus or minus 5 mils below cutting edge 14. The curvature of wall 15a is such that wall 15a represents about 1.5 radians of a circle. Floor 15b has a width of about 20 plus or minus 5 mils and wall 15c curves inwardly and upwardly along a less arcuate path than wall 15a to terminate some 25 plus or minus 10 mils from floor 15b. Thus recess 15 has a depth of about 25 mils, a floor of about 20 mils and an open top of about 70 mils. Thus it may be seen that only a portion of the circumference of a toothpick having a finished diameter of 60 miles will actually reside in the recess during the formation of toothpick as will be described. However, the configuration of the recess will determine how effectively the toothpicks are rolled and the distance between cutting edge 14 and the surface of shaft 11 must be at least as great as the distance of the diameter of the toothpick being produced.

Since tool 10 may be sized according to the desired dimensions of the toothpick being produced, it is not practical to limit the invention to a tool having any particular dimensions as they may be determined empirically from this description.

Figure 3:
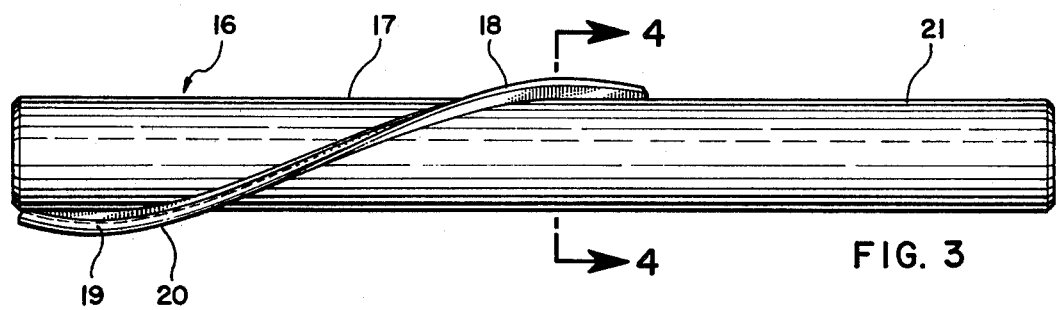
FIG. 3 is an elevational view of a cutting tool having a helical cutting lip.
Figure 4:
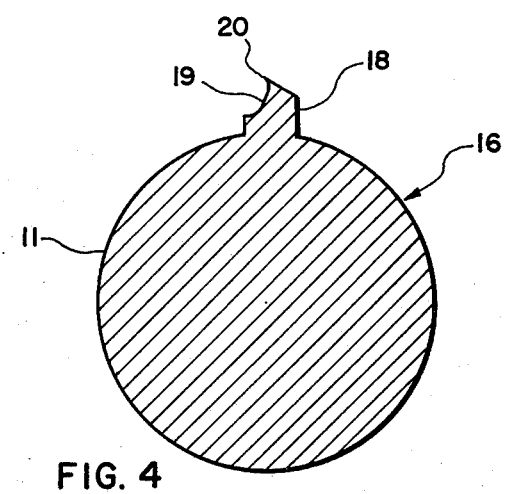
FIG. 4 is a cross-sectional view of the tool of FIG. 3 taken along lines 4—4 showing the cutting edge and lip recess.

FIGS. 3 and 4 show a tool 16 comprising a shaft 17 having a helical cutting lip 18 having a recess 19 resuming the length of the lip immediately adjacent cutting edge 20. The upper end 21 of tool 16 is adapted to fit into the chuck of a miling machine. The diameter of tool 16 and recess 19 are the same as or similar to those specified for tool 10.

Tools 10 and 16 may be made of any high carbon steel or alloy such as is already of use in the art of cutting and shaping polyethylene and similar plastics. Cutting lips 12 and 18 may be an integral part of tools 10 and 16 or may be separate from and secured into a chuck in the tools by fastening means such as screws. FIG. 2 shows a divided shaft 11 wherein cutting lip 12 is secured by screw 11a.

Without specifically illustrating the shape of the toothpicks, FIGS. 5a to 53 show how the cutting lips 12 and 18 function to simultaneously cut and roll films of plastic into toothpicks. Since the function is the same for both tools 10 and 16, the cutting operation will be described with reference to tool 10 only. However, the description will also apply to the operation of tool 16.

Tool 10 rotates at a high rate of speed, generally from about 1000 to 4000 rpm, and the depth at which the plastic block 22 approaches the tool. As shown by phantom line 23, the pattern of cut is in the shape of a thin crescent with the depth of cut being greater at the center than at the edges. The depth of cut will generally vary from about 0.5 mil at the edges to 5 mils at the center.

As cutting lip 12 contacts the plastic block 22 as shown in FIG. 5a, the cutting edge 14 begins to slice a thin film of plastic which enters recess 15 and begins to curl in an opposite direction. As the tool continues to rotate as shown in FIG. 5b through 5e, the plastic curls and is rolled within recess 15. As the cutting lip rotates out of the plastic block, the plastic film is completely severed and is ejected from recess 15 in its rolled form by centrifugal force.

Plastics such as polyethylene are sufficiently self lubricating that the overlapping layers of plastic film slip past each other during the rolling process into an even tightening roll. Moreover, the plastic film has a memory such that it becomes oriented to the tightly rolled position and remains in that position until physically unrolled.

The shaping of a toothpick and the tapering of the ends are functions of the angle at which the plastic film is severed from the solid plastic block. This angle will vary according to the type of cutting tool used. Hence, the cutting operation using tools 10 and 16 will be separately described.

Figure 6:
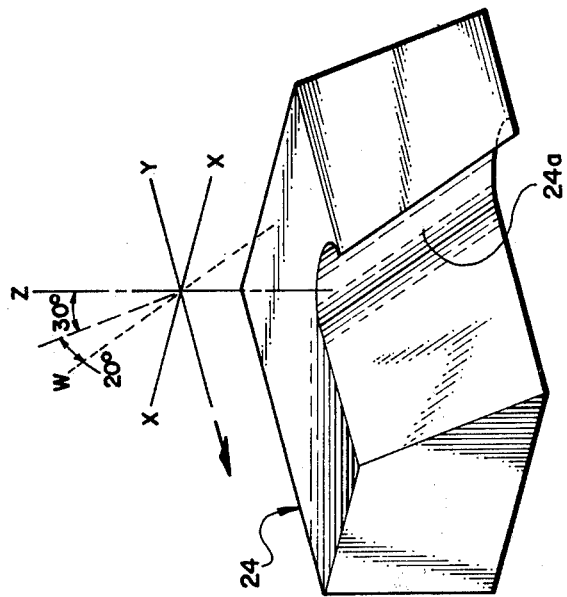
FIG. 6 is a perspective view of a block of solid plastic showing the general angle at which the cutting tool shown in FIG. 1 cuts from the block.

FIG. 6 shows a block of plastic 24 horizontally oriented to travel along the y axis of a pair of intersecting x, y rectangular coordinates. Area 24a shows the general angle at which tool 10 would cut into block 24. The tool 10 is initially placed in a vertical position identified as a z axis intersecting the x, y horizontal coordinates in a three dimensional system. Tool 10 is then rotated about 10 to 50 degrees counter clockwise in such a system toward the x axis and the ends of tool 10 are then rotated horizontally about 10 to 30 degrees counter clockwise from the x axis toward the y axis to form cutting axis w. When thus positioned, the lower portion of the cutting tool is the first to start cutting into a block of plastic having a flat vertical leading edge. Preferably tool 10 is rotated about 30 degrees toward the x axis from the z axis and the ends are then rotated about 20 degrees from the x axis toward the y axis to form cutting axis w as shown in FIG. 6.

With tool 10 thus positioned along cutting axis w of the three dimensional system, the cutting lip 12 cuts a parallelogram shaped film from block 24. FIGS. 7a to 7e depict the various stages of cutting and rolling which would occur during the rotation of cutting lip 12 through area 24a to produce a toothpick 25. Since cutting lip 12 is linear, the cutting angle w produces a parallel roll from side 26 toward side 27. The upper portion of side 26 becomes the forwardmost point of toothpick 25 because the angle between side edge 26 and the top edge 28 is acute. Thus, top edge 28 spirals backwardly along the toothpick body as it is rolled forming a tapered and layered front portion to the toothpick. The first curl formed in recess 15 by cutting edge 14 slicing into the plastic block 24 becomes a hollow central core extending the length of the toothpick.

Figure 8:
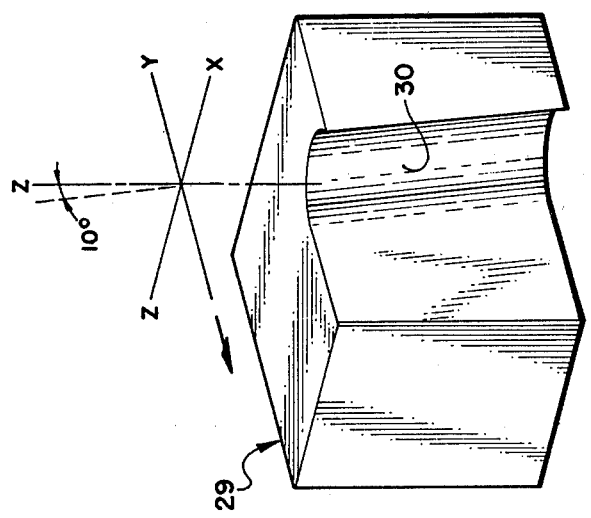
FIG. 8 is a perspective view of a block of solid plastic showing the general angle at which the helical cutting tool shown in FIG. 3 cuts from the block.
Figure 7E:
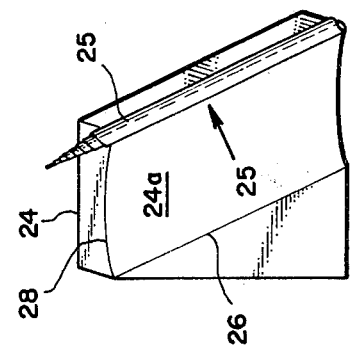
FIGS. 7a to 7e is schematic step by step representation coinciding with FIGS. 5a to 5e showing how a linear cutting tool as shown in FIG. 1 cutting in the plastic block shown in FIG. 6 produces a toothpick which is rolled and tapered at the forward end.
Figure 7D:
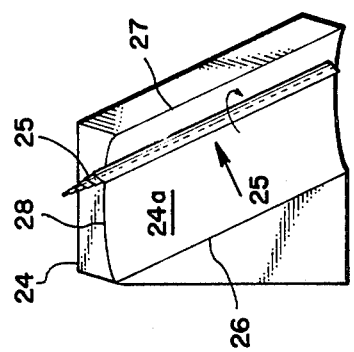
Figure 7C:
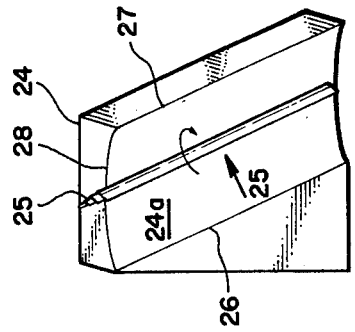
Figure 7B:
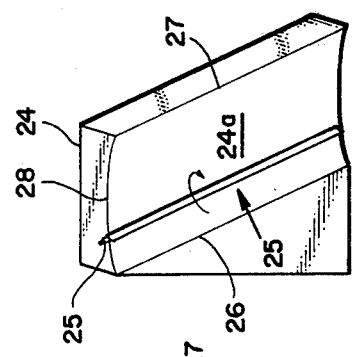
Figure 7A:
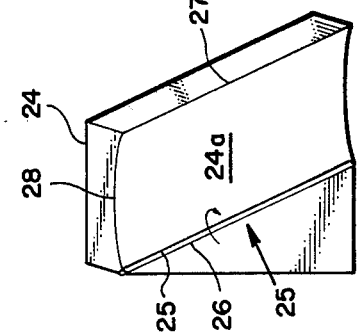

FIG. 8 shows a block of plastic 29 horizontally oriented to travel along the y axis of a pair of intersecting x, y horizontal coordinates lying in a common plane. Area 30 shows the surface into which tool 16 cuts into block 29. Tool 16 may be placed in a vertical z axis intersecting the x, y coordinates in a three dimensional system and may be rotated up to 10 degrees in either direction out of the z axis toward the y axis. However, such rotation is not essential as the angle at which toothpicks are made is determined by the angle at which cutting lip 18 spirals about the shaft 17 of tool 16. The angle of spiral of cutting lip 18 about shaft is about 20 to 40 degrees away from the longitudinal axis of tool 16 with angles of about 30 degrees being preferred.

With tool 16 vertically positioned, the cutting lip 18 cuts a rectangular shaped film which is angularly rolled from block 29.

FIGS. 9a to 9e depict the various stages of cutting and rolling which occur during the rotation of cutting lip 18 through area 30 to produce toothpick 31 which is tapered at both ends. Because cutting lip 18 is helical, the cutting edge 20 slices into block 29 at the juncture of side 32 and top edge 33 of area 30 and produces an angular roll toward opposite side 34. The angle of roll is the same as the angle of spiral of cutting lip 18.

Because the angle of roll is less than about 40 degrees and since the film cut from the plastic block is rectangular with the longest sides being sides 32 and 34, the last portion of the film to be rolled is the area adjacent the juncture of side 34 and bottom 35. Thus, bottom edge 35 forms a spiraling tapering ridge along what becomes the forward operation of toothpick 31. Side 34 also forms a ridge which spirals along the backward portion of the toothpick. There is also a continuous hollow central core running the length of the toothpick.

Various modifications may be made to the cutting tool which will not alter the function but which will affect the shape of the toothpick produced. For example, the cutting edges of the tools can be serrated. The resulting toothpick would thus have a corrugated film surface. Other modifications will also be obvious to those skilled in the art. The invention is, therefore, to be limited in scope only by the appended claims.

I claim:

1. A method of producing a rolled and layered toothpick having a forwardly tapered front portion and hollow central cavity from a thin plastic film which comprises the step of:
    (a) orienting a block of plastic of a predetermined thickness in a movable position along a fixed plane
    (b) positioning a cutting tool comprising a generally rotatable cylindrical shaft containing a single cutting lip on the shaft wherein the cutting lip has a single cutting edge and a recess immediately adjacent said cutting edge, said tool being attached to means for rapidly rotating said tool in a fixed plane relative to said plastic block
    (c) causing said tool to rotate rapidly, and
    (d) moving said plastic block along said predetermined plane into contact with said rapidly rotating tool at a fixed rate of speed wherein for each complete revolution of said tool the cutting edge on said cutting lip severs from said block a plastic film having a thickness of from about 0.5 to 5.0 mils causing said severed film to enter into said cutting lip recess and be rolled therein by the rotation of said tool into a toothpick which is ejected from said tool as the cutting lip rotates out of contact with said plastic block.

2. A method according to claim 1 wherein the recess in the cutting tool adjacent the cutting edge has curved sidewalls and a flat floor.

3. A method according to claim 2 wherein the cutting tool, the curvature of the sidewall adjacent the cutting edge is greater than the curvature of the opposite sidewall.

4. A method according to claim 2 wherein the cutting lip located on the shaft of the cutting tool is linear.

5. A method according to claim 4 wherein the plastic block is firmly oriented in a plane along the x, y coordinates of a three dimensional x, y, z rectangular coordinate system and movable along the y axis and wherein the cutting tool is attached to the rotating means such that the longitudinal axis of the tool is situated within the x, y, z system angled about 10 to 50 degrees from the z axis toward the x axis and about 10 to 30 degrees from the x axis toward the y axis with the lower portion of the cutting lip of the tool being the first portion of the tool to touch the plastic block as said block is first brought into contact with said tool.

6. A method according to claim 5 wherein the longitudinal axis of the cutting tool is situated within the x, y, z system angled about 30 degrees from the z axis toward the x axis and about 20 degrees from the x axis toward the y axis.

7. A method according to claim 5 wherein the plastic block has a thickness of about 1½ to 2½ inches, the diameter of the cutting tool is about 0.8 to 1.0 inches and the diameter of the recess adjacent the cutting edge of the cutting lip is about 40 to 70 mils.

8. A method according to claim 2 wherein the cutting lip located on the shaft of the cutting tool is helical.

9. A method according to claim 8 wherein the plastic block has a thickness of about 1½ to 2½ inches, the diameter of the cutting tool is about 0.8 to 1.0 inches and the diameter of the recess adjacent the cutting edge of the cutting lip is about 40 to 70 mils.

* * * * *